United States Patent
Coulthard et al.

(10) Patent No.: US 9,669,139 B2
(45) Date of Patent: Jun. 6, 2017

(54) FLUID COLLECTION CANISTER WITH INTEGRATED MOISTURE TRAP

(71) Applicant: KCI Licensing, Inc., San Antonio, TX (US)

(72) Inventors: Richard Daniel John Coulthard, Verwood (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 297 days.

(21) Appl. No.: 14/186,808

(22) Filed: Feb. 21, 2014

(65) Prior Publication Data

US 2014/0316358 A1    Oct. 23, 2014

Related U.S. Application Data

(60) Provisional application No. 61/784,734, filed on Mar. 14, 2013.

(51) Int. Cl.
*A61M 1/00* (2006.01)
*B01D 5/00* (2006.01)
(Continued)

(52) U.S. Cl.
CPC ........ *A61M 1/0049* (2013.01); *A61M 1/0052* (2014.02); *A61M 1/0088* (2013.01); *A61M 2205/7527* (2013.01); *A61M 2207/00* (2013.01); *B01D 5/0003* (2013.01); *B01D 5/0006* (2013.01); *B01D 5/0015* (2013.01);
(Continued)

(58) Field of Classification Search
CPC .............. A61M 1/0049; A61M 1/0088; A61M 1/0052; A61M 2207/00; A61M 2205/7527; F16T 1/34; F16T 1/36; B01D 45/08; B01D 45/06; B01D 45/10; B01D 47/027; B01D 5/0003; B01D 5/0006; B01D 5/0015; F02M 35/022; F02M 35/0226; F01M 2013/0433;
(Continued)

(56) References Cited

U.S. PATENT DOCUMENTS 1,355,846 A    10/1920 Rannells
2,402,140 A *   6/1946 Heintzelman .......... F24F 3/1411
                                                      55/419
(Continued)

FOREIGN PATENT DOCUMENTS

AU    550575 A1    3/1986
AU    745271       4/1999
(Continued)

OTHER PUBLICATIONS

International Search Report and Written Opinion for corresponding PCT/US2014/017755 mailed Aug. 8, 2014.
(Continued)

*Primary Examiner* — Adam Marcetich

(57) ABSTRACT

A moisture trap for removing liquid from fluid from a tissue site treated with reduced pressure are described. The moisture trap may include a barrier adapted to be fluidly coupled to and define an indirect fluid path between a fluid reservoir and a reduced-pressure source. The barrier may have a hydrophilic surface. The moisture trap also may include a sump adapted to receive condensation from the barrier.

67 Claims, 6 Drawing Sheets

(51) Int. Cl.
   *F28F 13/18* (2006.01)
   *B01D 45/08* (2006.01)
(52) U.S. Cl.
   CPC ............ *B01D 5/0054* (2013.01); *B01D 45/08* (2013.01); *F28F 13/187* (2013.01)
(58) Field of Classification Search
   CPC ... F01M 2013/0438; F01M 2013/0461; F01M 2013/0477; F01M 2013/0488
   See application file for complete search history.

(56) References Cited

U.S. PATENT DOCUMENTS

| | | | |
|---|---|---|---|
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,739,553 | A * | 6/1973 | Aine ........... B01D 53/22 55/DIG. 30 |
| 3,826,254 | A | 7/1974 | Mellor |
| 3,892,550 | A * | 7/1975 | Riis ........... B01D 5/0045 266/152 |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,202,778 | A * | 5/1980 | Middelbeek ....... B01D 17/0211 210/522 |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A * | 8/1984 | Kashmer ............ A61M 1/0052 128/205.12 |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,000,768 | A * | 3/1991 | Hwang ................. F01N 3/0211 55/308 |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,460,147 | A * | 10/1995 | Bohl ..................... B01D 45/12 123/572 |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 5,985,004 | A * | 11/1999 | Boyd .................... B01D 1/305 55/492 |
| 6,071,267 | A | 6/2000 | Zamierowski |
| 6,135,116 | A | 10/2000 | Vogel et al. |
| 6,241,747 | B1 | 6/2001 | Ruff |
| 6,267,804 | B1 * | 7/2001 | Marlowe ............... B01D 47/06 96/237 |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 8,002,712 | B2 * | 8/2011 | Meka ................... G01N 33/497 600/529 |
| 2001/0003892 | A1 * | 6/2001 | Rikyuu ................. B01D 45/08 55/315.2 |
| 2002/0020182 | A1 * | 2/2002 | Hauser .................. F24F 13/222 62/281 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0144600 | A1 * | 10/2002 | TeGrotenhuis ......... B01B 1/005 95/273 |
| 2003/0037730 | A1 * | 2/2003 | Yamasaki ............... C23C 16/18 118/715 |
| 2003/0150198 | A1 * | 8/2003 | Illingworth ............. A47L 5/24 55/406 |
| 2003/0163101 | A1 * | 8/2003 | Say ......................... A61M 1/0023 604/319 |
| 2004/0109981 | A1 * | 6/2004 | Lawrence .............. B01D 1/305 428/141 |
| 2005/0000199 | A1 * | 1/2005 | Carter .................. F24C 15/2035 55/442 |
| 2005/0161030 | A1 * | 7/2005 | Roberts ................ F02M 25/06 123/572 |
| 2006/0064991 | A1 * | 3/2006 | Kozak .................. B60H 1/00028 62/93 |

(56) References Cited

U.S. PATENT DOCUMENTS

| | | | |
|---|---|---|---|
| 2006/0079852 A1 | 4/2006 | Bubb et al. | |
| 2006/0112709 A1* | 6/2006 | Boyle | B01D 5/0015 62/272 |
| 2007/0295315 A1* | 12/2007 | Guerry | F01M 13/04 123/572 |
| 2008/0034966 A1* | 2/2008 | Kesten | B01D 53/229 95/52 |
| 2008/0149082 A1* | 6/2008 | Heed | F01M 13/04 123/573 |
| 2008/0210279 A1* | 9/2008 | Hildenbrand | A47L 15/0081 134/56 D |
| 2008/0236116 A1* | 10/2008 | Kawasaki | B01D 45/06 55/385.4 |
| 2009/0071189 A1* | 3/2009 | Martins | F25B 39/04 62/506 |
| 2009/0126575 A1* | 5/2009 | Son | F01M 13/0011 96/189 |
| 2009/0221990 A1* | 9/2009 | Jaeb | A61M 1/0001 604/540 |
| 2010/0126479 A1* | 5/2010 | Shieh | F01M 13/04 123/573 |
| 2010/0293905 A1* | 11/2010 | Lin | F02M 25/089 55/325 |
| 2011/0167774 A1* | 7/2011 | Herman | F16L 55/24 55/423 |
| 2011/0197764 A1* | 8/2011 | Ardizzone | B01D 45/08 95/272 |
| 2011/0288512 A1 | 11/2011 | Locke et al. | |
| 2012/0132075 A1* | 5/2012 | Jarrier | B01D 46/0023 95/268 |
| 2013/0170142 A1* | 7/2013 | Weaver, Jr. | H01L 23/427 361/701 |
| 2013/0251948 A1* | 9/2013 | Lyons | B32B 5/16 428/148 |
| 2013/0295315 A1* | 11/2013 | Durdag | D04H 1/4326 428/76 |
| 2014/0109533 A1* | 4/2014 | Horiuchi | F01M 13/04 55/430 |
| 2014/0182456 A1* | 7/2014 | Chou | B01D 45/08 96/239 |

FOREIGN PATENT DOCUMENTS

| | | |
|---|---|---|
| AU | 755496 | 2/2002 |
| AU | 2012201896 A1 | 4/2012 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1512452 A1 | 3/2005 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistula"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

(56) References Cited

OTHER PUBLICATIONS

Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

\* cited by examiner

FLUID COLLECTION CANISTER WITH INTEGRATED MOISTURE TRAP

Under 35 U.S.C. §119(e), this application claims priority to and the benefit of U.S. Provisional Patent Application No. 61/784,734 filed Mar. 14, 2013, entitled "Wound Fluid Collection Canister with Integrated Condensation Inhibitor," the disclosure of which is hereby incorporated by reference in its entirety.

TECHNICAL FIELD

The present disclosure relates generally to medical treatment systems for treating tissue sites and processing fluids. More particularly, but not by way of limitation, the present disclosure relates to a canister having a device for the removal of liquid from a fluid.

BACKGROUND

Clinical studies and practice have shown that reducing pressure in proximity to a tissue site can augment and accelerate growth of new tissue at the tissue site. The applications of this phenomenon are numerous, but is has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," "negative pressure wound therapy," and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

According to an illustrative embodiment, a system for treating a tissue site with reduced pressure is described. The system may include a dressing adapted to be placed adjacent to the tissue site and a canister having a fluid reservoir adapted to be fluidly coupled to the dressing. A moisture trap may be fluidly coupled to the fluid reservoir. The moisture trap may include a barrier and a sump adapted to receive condensation from the barrier. A reduced-pressure source may be adapted to be fluidly coupled to the moisture trap. The barrier may include a hydrophilic surface and define an indirect fluid path between the fluid reservoir and the reduced-pressure source.

According to another illustrative embodiment, a moisture trap for removing liquid from fluids from a tissue site treated with reduced pressure is described. The moisture trap may include a barrier adapted to be fluidly coupled to and define an indirect fluid path between a fluid reservoir and a reduced-pressure source. The barrier may have a hydrophilic surface. The moisture trap also may include a sump adapted to receive condensation from the barrier.

According to yet another illustrative embodiment, a method for treating a tissue site with reduced pressure is described. A reduced-pressure dressing may be disposed adjacent to the tissue site and fluidly couple a reduced-pressure source to the reduced-pressure dressing. Reduced pressure can be supplied to the reduced-pressure dressing with the reduced-pressure source, and fluid may be drawn from the tissue site with the reduced-pressure dressing and the reduced-pressure source. The fluid may be collected in a fluid reservoir in a canister fluidly coupled between the reduced-pressure dressing and the reduced-pressure source. The fluid may be moved through an indirect fluid path that may be fluidly coupled between the canister and the reduced-pressure source. The indirect fluid path may be formed by a barrier having a hydrophilic surface to condense liquids from the fluids. The condensed liquid may be channeled from the hydrophilic surface to a sump to store the condensed liquids.

According to still another illustrative embodiment, a method of manufacturing a moisture trap for removing liquid from fluids from a tissue site treated with reduced pressure is described. A barrier may be adapted to be fluidly coupled between a fluid reservoir and a reduced-pressure source, the barrier having a hydrophilic surface. The barrier may be positioned between the fluid reservoir and the reduced-pressure source to define an indirect fluid path. A sump may be provided and adapted to receive condensation from the barrier.

Other aspects, features, and advantages of the illustrative embodiments will become apparent with reference to the drawings and detailed description that follow.

DETAILED DESCRIPTION OF ILLUSTRATIVE EMBODIMENTS

New and useful systems, methods, and apparatuses for removing liquid from fluid drawn from a tissue site in a reduced-pressure therapy environment are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context, and reference to "an" item generally refers to one or more of those items. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
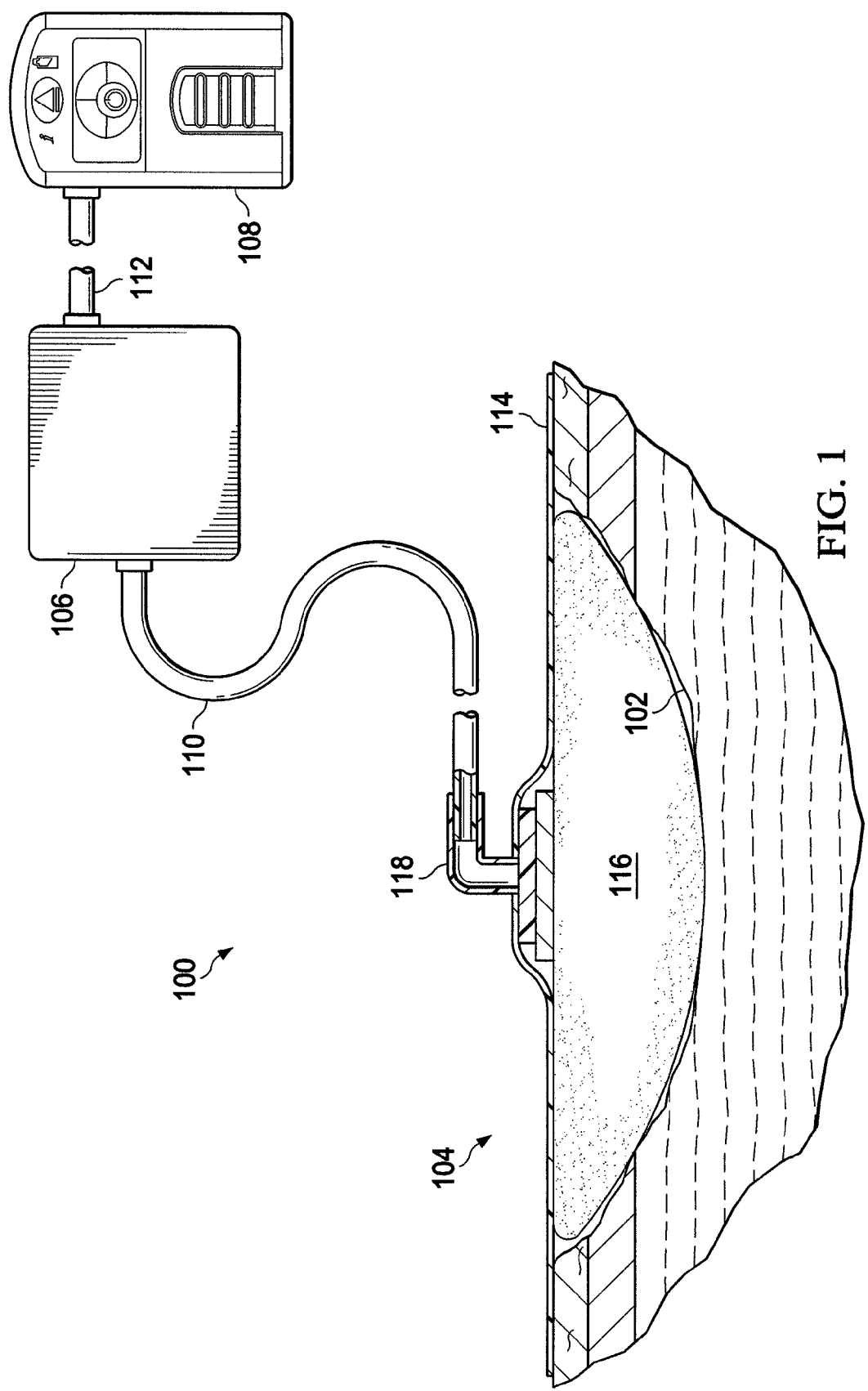
FIG. 1 is sectional view illustrating an exemplary embodiment of a reduced-pressure therapy system in accordance with this specification.

FIG. 1 is a sectional view of one embodiment of a therapy system 100 for supplying reduced pressure to a tissue site 102 that can remove liquid from fluid drawn from the tissue site 102. As illustrated, the therapy system 100 may include a dressing 104, a canister 106, and a reduced-pressure source 108. The dressing 104, the canister 106, and the reduced-pressure source 108 may be fluidly coupled by one or more conduits, such as a tube 110 fluidly coupling the dressing 104 to the canister 106, and a tube 112 fluidly coupling the canister 106 to the reduced-pressure source 108.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

In general, components of the therapy system 100 may be coupled directly or indirectly. For example, reduced-pressure source 108 may be directly coupled to the canister 106 and indirectly coupled to the dressing 104 through the canister 106. Components may be fluidly coupled to each other to provide a path for transferring fluids (i.e., liquid and/or gas) between the components. In some embodiments, components may be fluidly coupled with the tube 110 and the tube 112, for example. A "tube," as used herein, broadly refers to a tube, pipe, hose, conduit, or other structure with one or more lumina adapted to convey fluids between two ends. Typically, a tube may be an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation may generally be presumed for purposes of describing various features and components of reduced-pressure therapy systems herein. Thus, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, the fluid path may also be reversed in some applications (such as by substituting a positive-pressure source for a reduced-pressure source) and this descriptive convention should not be construed as a limiting convention.

"Reduced pressure" generally refers to a pressure less than a local ambient pressure, such as the ambient pressure in a local environment external to a sealed therapeutic environment provided by the dressing 104. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The dressing 104 generally may include a cover, such as a drape 114, a tissue interface, such as a manifold 116, and a connector, such as an adapter 118. In operation, the manifold 116 may be placed within, over, on, or otherwise proximate to a tissue site, such as the tissue site 102. The drape 114 may be placed over the manifold 116 and sealed to tissue proximate to the tissue site 102. The tissue proximate to the tissue site 102 is often undamaged epidermis peripheral to the tissue site 102. Thus, the dressing 104 can provide a sealed therapeutic environment proximate to the tissue site 102 that may be substantially isolated from the external environment, and the reduced-pressure source 108 can reduce the pressure in the sealed therapeutic environment. Reduced pressure applied across the tissue site 102 through the manifold 116 in the sealed therapeutic environment can induce macrostrain and microstrain in the tissue site 102, as well as remove exudates and other fluids from the tissue site 102. Exudate and other fluid from the tissue site 102 can be collected in the canister 106 and disposed of properly.

The drape 114 may be an example of a sealing member. A sealing member may be constructed from a material that can provide a fluid seal between two components or two environments, such as between a therapeutic environment and a local external environment. The sealing member may be, for example, an impermeable or semi-permeable elastomeric material that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically acceptable, pressure-sensitive adhesive that may extend about a periphery, a portion of, or an entirety of the sealing member. Other example embodiments of an attachment device may include a double-sided tape, paste, hydrocolloid, hydrogel, silicone gel, organogel, or an acrylic adhesive.

The manifold 116 can be generally adapted to contact the tissue site 102. The manifold may be partially or fully in contact with the tissue site 102. If the tissue site 102 is a wound, for example, the manifold 116 may partially or completely fill the wound, or may be placed over the wound. The manifold 116 may take many forms, and may have many sizes, shapes, or thicknesses depending on a variety of factors, such as the type of treatment being implemented or the nature and size of the tissue site 102. For example, the size and shape of the manifold 116 may be adapted to the contours of deep and irregular shaped tissue sites.

More generally, a manifold may be a substance or structure adapted to distribute reduced pressure across a tissue site, remove fluids from across a tissue site, or distribute reduced pressure and remove fluids across a tissue site. In some embodiments, a manifold may also facilitate delivering fluids to a tissue site, if the fluid path is reversed or a secondary fluid path is provided, for example. A manifold may include liquid channels or pathways that distribute fluids provided to and removed from a tissue site around the manifold. In some illustrative embodiments, the liquid channels or pathways may be interconnected to improve distribution or removal of fluids across a tissue site. For example, cellular foam, open-cell foam, porous tissue collections, and other porous material, such as gauze or felted mat, generally include structural elements arranged to form liquid channels. Liquids, gels, and other foams may also include or be cured to include liquid channels.

In one illustrative embodiment, the manifold 116 may be a porous foam material having interconnected cells or pores adapted to distribute reduced pressure across the tissue site 102. The foam material may be either hydrophobic or hydrophilic. In one non-limiting example, the manifold 116 can be an open-cell, reticulated polyurethane foam such as GranuFoam® dressing available from Kinetic Concepts, Inc. of San Antonio, Tex.

In an example in which the manifold 116 may be made from a hydrophilic material, the manifold 116 may also wick fluid away from the tissue site 102, while continuing to distribute reduced pressure to the tissue site 102. The wicking properties of the manifold 116 may draw fluid away from the tissue site 102 by capillary flow or other wicking mechanisms. An example of a hydrophilic foam may be a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 116 may further promote granulation at the tissue site 102 if pressure within the sealed therapeutic environment is reduced. For example, any or all of the surfaces of the manifold 116 may have an uneven, coarse, or jagged profile that can induce microstrains and stresses at the tissue site 102 if reduced pressure is applied through the manifold 116.

In one embodiment, the manifold may be constructed from bioresorable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 116 may further serve as a scaffold for new cell-growth, or a scaffold material may be used in conjunction with the manifold 116 to promote cell-growth. A scaffold is generally a substance or structure used to enhance or promote the growth of cells or formation of tissue; such as a three-dimensional porous structure that provides a template for cell growth. Illustrative examples of scaffold materials include calcium phosphate, collagen, PLA/PGA, coral hydroxy apatites, carbonates, or processed allograft materials.

A reduced-pressure source, such as the reduced-pressure source 108, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

The canister 106 may be representative of a container, canister, pouch, or other storage component that can be used to manage exudate and other fluid withdrawn from a tissue site. In many environments, a rigid container may be preferred or required for collecting, storing, and disposing of fluid. In other environments, fluid may be properly disposed of without rigid container storage, and a re-usable container could reduce waste and costs associated with reduced-pressure therapy. The canister 106 may be fluidly coupled to the dressing 104 with the tube 110 and fluidly coupled to the reduced-pressure source 108 with the tube 112. The reduced-pressure source 108 supplies reduced pressure to the canister 106 through the tube 112 and to the dressing 104 through the canister 106 and the tube 110. In this manner, the reduced-pressure source 108 may draw fluid, including exudate from the tissue site 102 into the canister 106.

During operation of a reduced-pressure therapy system, a reduced-pressure source may draw fluid from a tissue site into a canister, such as the canister 106. The fluid drawn from a tissue site may have a high content of evaporated liquid, giving the fluid a high relative humidity. If a canister is coupled to a tissue site through a tube, as in therapy system 100, a portion of the evaporated liquid may condense in the tube. This may occur due to the cooler ambient environment surrounding the tube, for example. The fluid, including the condensed liquid in the tube, may be drawn into the canister by the reduced-pressure source.

Once the fluid reaches a canister, additional liquid may condense from the fluid in the canister. Despite the condensation, the fluids in a canister may have a relative humidity as high as about 70%, for example. This relative humidity depends, in part, on the ambient temperature around a canister, the location of the canister, the orientation of the canister, how much liquid may be in the canister, and the type of liquid, including exudate, in the canister.

If a canister is coupled to a reduced-pressure source through another tube, as in therapy system 100, humid fluid may also be drawn from a canister into the tube coupled to the reduced-pressure source. There, further liquid may condense from the fluid in the tube. The condensed liquid in the tube may be drawn into the reduced-pressure source, which may cause the reduced-pressure source to operate improperly or stop functioning altogether.

In other embodiments, a canister and reduced-pressure source may be jointly housed within an integral therapy unit. These units may face problems similar to those described above, as highly humid fluid may be drawn from the canister into the reduced-pressure source.

To address this problem, some canisters may expel the highly humid fluid onto an inside face of the canister before drawing the fluid into a reduced-pressure source. There, the fluid can cool and liquid may condense out of the fluid. The condensation on the inside face of the canister may cause the canister to appear to be leaking. Other canisters expel fluid from the canister into an internal location of a combined canister and reduced-pressure source unit. In these canisters, liquid can condense from the fluids within this structure and can cause the canister to appear to be contaminated. Condensed liquid within the structure may also lead to the growth of flora. Growth of flora within the structure may lead to growth of flora elsewhere in a therapy system that may be detrimental to the health of the person receiving reduced-pressure therapy. Still other canisters may expel the fluid directly into a pump chamber of a reduced-pressure source. Condensed liquid in a pump chamber can cause failure of pump seals, failure of electrical connections within the pump, and a reduced ability to provide reduced-pressure therapy. Systems having a higher fluid flow tolerance may experience a magnification of the problems described above.

As disclosed herein, the therapy system 100 can overcome these shortcomings and others by providing a moisture trap associated with the canister that can reduce the liquid content of fluid leaving the canister 106. For example, in some embodiments of the therapy system 100, a moisture trap may be fluidly coupled between a fluid reservoir of the canister 106 and a reduced-pressure source 108. At least one barrier may be disposed within some embodiments of the moisture trap, providing an indirect fluid path between the fluid reservoir and the reduced-pressure source 108. The barrier preferably comprises a hydrophilic material or a hydrophilic surface. A sump may also be disposed within the moisture trap in fluid communication with the barrier to receive liquid condensed thereon.

Figure 2:
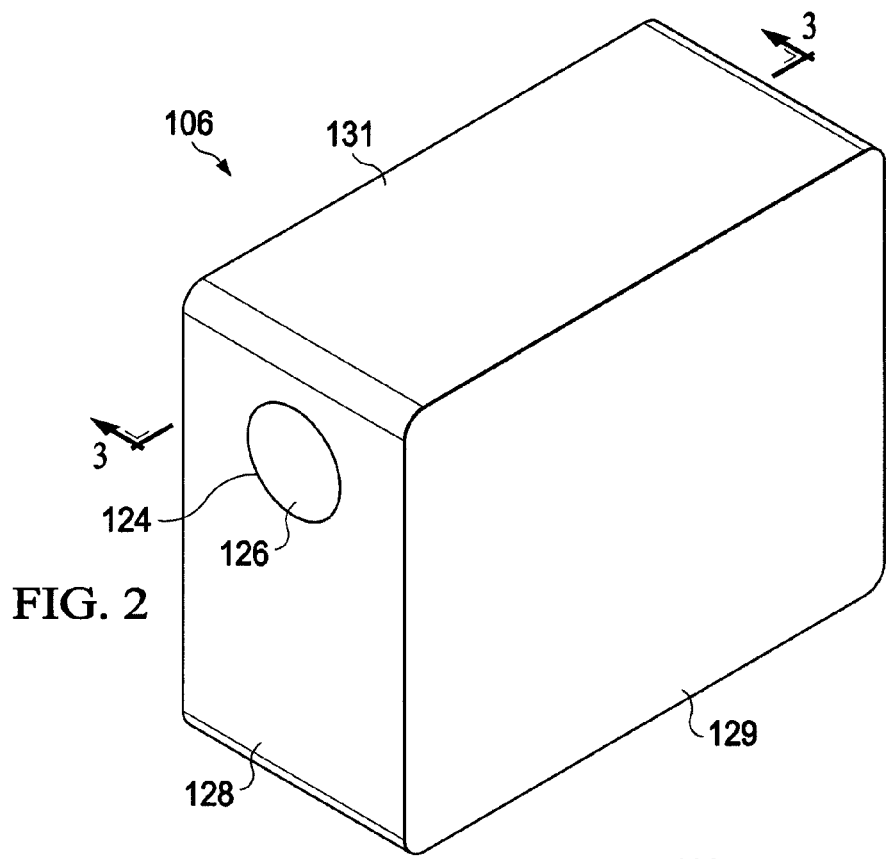
FIG. 2 is a perspective view of an illustrative canister of the reduced-pressure therapy system of FIG. 1.

FIG. 2 is a perspective view illustrating additional details that may be associated with an example embodiment of the canister 106. As shown, the canister 106 may include a fluid outlet, such as an opening 124, and a filter 126 disposed within the opening 124. The filter 126 may be a hydrophobic filter, for example, configured to limit or reduce the number of particulates, including liquids, passing through the opening 124. In some embodiments, an adapter or connector (not shown) may be disposed over the opening 124 to facilitate coupling between the opening 124 and a tube, such as the tube 112. The canister 106 may also include three pairs of opposing walls, such as, end walls 128, side walls 129, and top and bottom walls 131.

Figure 3:
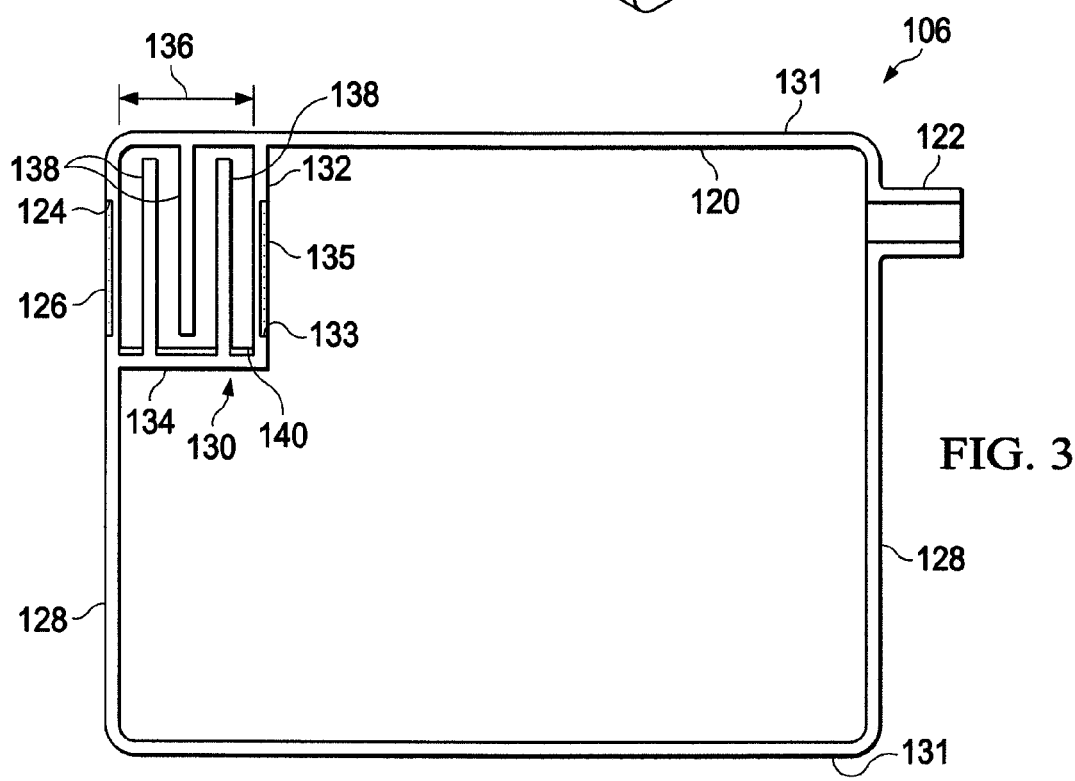
FIG. 3 is a sectional view of the canister of FIG. 2 having a moisture trap.

FIG. 3 is a sectional view illustrating additional details that may be associated with example embodiments of the canister 106. As shown in FIG. 3, the canister 106 may also include a fluid inlet, such as port 122. The port 122 may facilitate coupling the canister 106 to a tube, such as the tube 110. In other embodiments, the opening 124 and the port 122 may be located on other portions of the canister 106.

As illustrated in the example embodiment of FIG. 2, the end walls 128, the side walls 129, and the top and bottom walls 131 form a six-sided body. The end walls 128, the side walls 129, and the top and bottom walls 131 each join adjacent walls at an approximately ninety degree angle. In other exemplary embodiments, the canister 106 may have flexible walls or other shapes, for example, spherical or pyramidal.

As shown, the end walls 128 couple to the top and bottom walls 131 and the side walls 129 to form a fluid reservoir 120. The illustrative canister 106 also may include a moisture trap 130. The moisture trap 130 in this example embodiment may be fluidly coupled between the fluid reservoir 120 and the reduced-pressure source 108. As illustrated, for example, the moisture trap 130 can be disposed within the canister 106 proximate to the opening 124 so that fluid flowing from the fluid reservoir 120 passes through the moisture trap 130 before passing through the opening 124.

The moisture trap 130 generally may include a first wall 132, a second wall 134, and at least one fluid barrier, such as a plate 138. As illustrated in FIG. 3, the first wall 132 and the second wall 134 can join at ends of each wall at an angle of approximately 90 degrees. The first wall 132 and the second wall 134 may be joined at opposite ends to the walls of the canister 106 that form the fluid reservoir 120. In some embodiments, the moisture trap 130 may be secured to or otherwise disposed adjacent to the opening 124 without joining the first wall 132 or the second wall 134 to the walls of the canister 106. The first wall 132 may generally be parallel to the opening 124 and separated from the opening 124 by a distance 136. The distance 136 may be a portion of a total length of the canister 106. In some embodiments, the distance 136 may extend a majority of the length of the canister 106. In other embodiments, the distance 136 may extend less than about one-half of the length of the canister 106. As illustrated, in some embodiments the second wall 134 may generally be perpendicular to the first wall 132. In the illustrated embodiment, the first wall 132 and the second wall 134 fluidly isolate a portion of the fluid reservoir 120 proximate to the opening 124 from the remaining portions of the fluid reservoir 120.

The first wall 132 may have an opening 133 similar to the opening 124, as illustrated in FIG. 3. The opening 133 can permit fluid communication between the fluid reservoir 120 and the moisture trap 130. A filter 135 may be disposed within the opening 133. The filter 135 may be similar to the filter 126 and may be a hydrophobic filter configured to limit or reduce the number of particulates, including liquids, passing through the opening 133.

As illustrated in FIG. 3, the moisture trap 130 may also include a sump, such as the sump 140. In some embodiments, the sump 140 may be disposed adjacent to the second wall 134 and perpendicular to the first wall 132, as illustrated. The sump 140 may consist of or include a layer of material having a thickness less than a height of the first wall 132 and may extend the width of the moisture trap 130 between the side walls 129 of the canister 106. For example, the sump 140 may include an absorbent material disposed within the moisture trap 130 to collect liquid condensed from fluid flowing through the moisture trap 130. In some embodiments, the thickness of the absorbent material may vary as needed for the particular application of the moisture trap 130. In some embodiments, the sump 140 may extend only a portion of the width of the moisture trap 130 to allow the sump 140 to expand as the sump 140 receives liquid, for example. In the illustrative embodiment of FIG. 3, the sump 140 may be fluidly isolated from the fluid reservoir 120 so that liquid in the fluid reservoir 120 may not interact with the sump 140.

The liquid condensed from the fluid flowing through the moisture trap 130 may primarily be water, making materials formed of super absorbent polymers suitable for efficient use as the sump 140. In some embodiments the sump 140 may be sodium polyacrylate. In other embodiments, the sump 140 may be BASF Luquasorb® or Luquafleece® 402C; Technical Absorbents Limited superabsorbent fibers, such as TAL 2327; Texsus spa FP2325; or an isolyser. In still other embodiments, the sump 140 may be an absorbent having carboxymethyl cellulose or alginates.

As illustrated in FIG. 3, a fluid barrier can be disposed between the first wall 132 and the opening 124. A fluid barrier may be a device configured to impede, restrict, or otherwise direct fluid flow. For example, the fluid barrier of FIG. 3 may include three plates 138 disposed in the fluid path between the opening 124 and the opening 133. A plate, such as the plate 138, may be a generally rectangular piece of material. In some embodiments, a plate may be a solid piece of rectangular material. Each plate 138 may have a first end that can be joined to a wall. As shown in FIG. 3, for example, a first plate 138 may have a first end that joins to the second wall 134; a second plate 138 may have a first end that joins to a wall forming a portion of the canister 106; and a third plate 138 may have a first end that joins to the second wall 134. Each plate 138 in this example embodiment may have a second end separated from the wall proximate to the second end. The separation may form a gap between the wall proximate to the second end and the second end of each plate 138. Sides of each plate 138 that are perpendicular to the first end and the second end may be joined to the side walls 129 forming the canister 106 and the fluid reservoir 120 so that fluid communication around each plate 138 may only occur across the second end of each plate 138.

Each plate 138 may be in a parallel juxtaposition, for example, each plate 138 may be positioned so that the plate 138 may be parallel to the first wall 132 and to adjacent plates 138. Each plate 138 may also be disposed within the moisture trap 130 and oriented so that a plane in which the plate 138 is disposed may intersect a plane in which the sump 140 is disposed. For example, the plates 138 may all be perpendicular to the sump 140 in some embodiments. In other embodiments, the plates 138 may not be perpendicular to the sump 140, but may also not be parallel to the sump 140. In the illustrated embodiment, the first end of a plate 138 proximate to the first wall 132 may be joined to the second wall 134 so that fluid passes between the second end of the plate 138 and the top wall of the top and bottom walls 131 forming an exterior of the canister 106.

The plate 138 proximate to the opening 124 may also be joined to the second wall 134 so that there may be a gap between the second end of the plate 138 and the top wall 131 forming the exterior of the canister 106. The plate 138 disposed near a center portion of the second wall 134 may be joined to the top wall 131 forming an exterior of the canister 106 so that there may be a gap between the second end of the plate 138 and the second wall 134. In this manner, the plates 138 form an indirect fluid path between the opening 133 and the opening 124. In this context, an "indirect" fluid path may be a fluid path between two locations having at least one change of direction between the two locations. An indirect fluid path may also be referred to as a "tortuous" fluid path, a "labyrinthine" fluid path, or a "convoluted" fluid path.

Figure 4A:
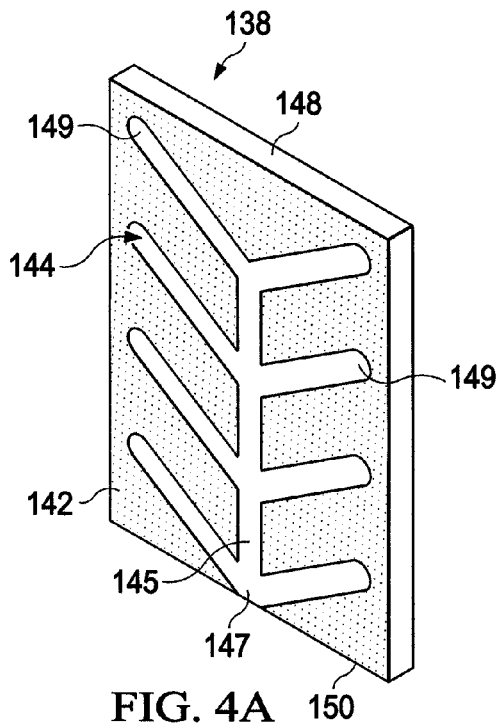
FIG. 4A is a perspective view of an illustrative plate of the moisture trap of FIG. 2.

FIG. 4A is a perspective view illustrating additional details that may be associated with some embodiments of the plates 138 of FIG. 3. As illustrated, the plate 138 may include one or more liquid channels 144 disposed on a surface of the plate 138, such as a condensation surface 142. A channel, such as the channel 144, may be a portion of the plate 138 configured to direct liquid by providing a preferential path for liquid flow. In some embodiments, the plate 138 may include the liquid channels 144 on both sides of the plate 138. The condensation surface 142 may be preferably a hydrophilic surface, either wholly or in part. A surface that is hydrophilic may be a surface treated with a material or formed from a material that is molecularly attractive to water. In the illustrated embodiments, the condensation surface 142 may be a portion of the plate 138 formed of a hydrophilic material or having a hydrophilic material disposed thereon.

Additionally or alternatively, the liquid channels 144 may be hydrophobic in some embodiments. Hydrophobic materials may be materials that are treated with or formed from a material that is molecularly repulsive to water. For example, the liquid channels 144 may be formed of a hydrophobic material or have a hydrophobic material disposed thereon, which may facilitate movement of liquid through the liquid channels 144. In the illustrated embodiment, the plate 138 may have a collection end 148 and a drainage end 150. The plate 138 may be oriented within the moisture trap 130 so that the drainage end 150 may be proximate to or adjacent to the sump 140. The liquid channels 144 may form pathways configured to direct condensed liquid toward the drainage end 150 and the sump 140. In the embodiment of FIG. 4A, for example, the liquid channels 144 include a central channel 145 proximate to a center portion of the plate 138, and the central channel 145 may have a terminus 147 proximate to the drainage end 150. Tributary channels 149 may extend from the edges of the plate 138 toward the central channel 145 and generally toward the drainage end 150 so that the liquid channels 144 form a fletching pattern. As illustrated, the tributary channels 149 in the example embodiment of FIG. 4A are generally configured to direct liquid from outer portions of the plate 138 toward the central channel 145. Preferably, the plate 138 may be oriented within the moisture trap 130 so that the liquid channels 144 may be aided by gravity.

Figure 4B:
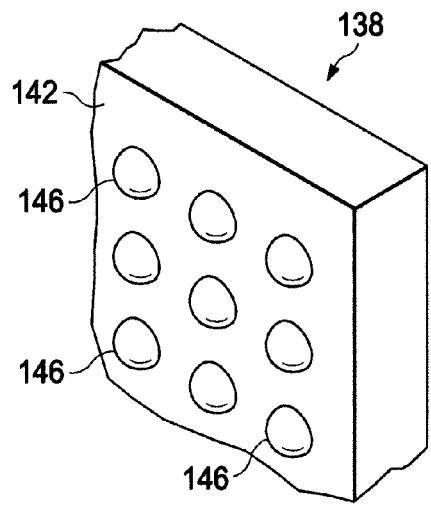
FIG. 4B is a detailed perspective view of a portion of the plate of FIG. 4A.

FIG. 4B is a detail perspective view illustrating additional details that may be associated with the example embodiment of the plate 138 illustrated in FIG. 4A. In some embodiments, the condensation surface 142 may have a rough finish. For example, the condensation surface 142 may have bumps, nodules, protuberances or other forms of protrusions, illustrated in FIG. 4B as protrusions 146. In some embodiments, the protrusions 146 may protrude between about 15 microns and about 20 microns from the surrounding condensation surface 142, and are also preferably hydrophilic. The protrusions 146 may be spherical, conical, pyramidal, grooves, other polygons, or may have an amorphous or irregular shape, for example. In some embodiments, the protrusions 146 may be formed by injection molding, stamping, hot or cold rolling, chemical and photo lithographic etching, micro machining, or bead, sand, or vapor blasting of the plate 138.

In some embodiments, the barrier in the moisture trap 130 may be a porous plate, mesh, net, or fabric that permits fluid to flow through it. The porous plate, mesh, net, or fabric forms an indirect fluid flow path as the porous plate, mesh, net, or fabric may impede the flow of fluid from the opening 133 to the opening 124. In addition, the porous plate, mesh, net, or fabric may be formed of a plurality of obstructions, such as the fibers of a woven fabric that may cause the fluid to change directions in response to interaction with the obstruction; thus, such obstructions form an indirect fluid path between the opening 133 and the opening 124. For example, if each plate 138 is a porous plate and extends from the top wall 131 to the second wall 134, then fluid can flow through the plate 138 rather than around the plate 138.

The porous plate, mesh, net, or fabric may be formed of a hydrophilic material, or be treated to impart hydrophilic properties to the material. In addition, the liquid channels 144 may be formed on the porous plate, mesh, net, or fabric. In some embodiments, the porous plate, mesh, net, or fabric may have a wax coating to form the liquid channels 144. In other embodiments, the liquid channels 144 may be formed on the porous plate, mesh, net, or fabric versions of the plate 138, for example, the area of the material where the liquid channels 144 are desired could be fused together and treated to impart hydrophobic properties. The porous plate, mesh, net, or fabric versions of the plate 138 may be formed from a woven or non-woven material, a foam, a sintered polymer or formed from a solid piece of material formed to have pores. Nets or meshes may be extruded or expanded to increase the flow area; however, the surface area available for condensation should be maximized. In addition, the porous plate, mesh, net, or fabric versions of the plate 138 may be stacked or layered with additional plates 138.

The plate 138 may be manufactured from a hydrophilic material, for example, and then treated to form the liquid channels 144. Formation of the liquid channels 144 may be accomplished by plasma coating, for example. In plasma coating, plasma may be used to deposit a thin coating of a compound designed to alter the level of hydrophilicity. For example, the plasma coating processes developed by P2i Limited may be used to form the liquid channels 144. In other embodiments, the plate 138 may be formed of a hydrophobic material. The plate 138 may then be treated to form the condensation surface 142. Formation of the condensation surface 142 may be done with a plasma coating process or a wet coating process, for example. In some embodiments, a wet coating process or a chemical vapor deposition process may be used to deposit Parylene to form the condensation surface 142. In other embodiments, a corona or plasma coating process may oxidize the surface of the plate 138 to form the condensation surface 142. Hydak® manufactured by Biocoat, Inc. may also be used to treat the plate 138 to form the condensation surface 142. In some embodiments, the plate 138 may not include the liquid channels 144. In these embodiments, the condensation surface 142 may encompass the entirety of the plate 138. Generally, in embodiments having both the condensation surface 142 and the liquid channels 144, the condensation surface 142 may be greater than or equal to about 80% of the plate 138.

Figure 5:
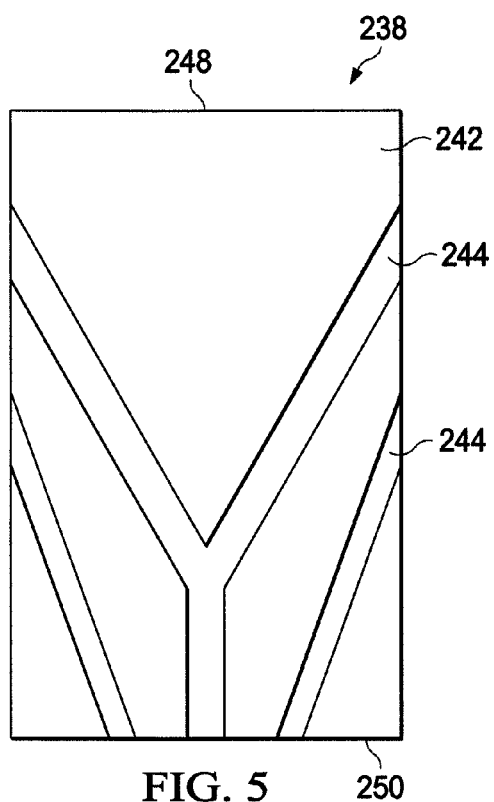
FIG. 5 is an elevation view of another embodiment of a plate of the moisture trap of FIG. 2.

FIG. 5 is a front view of another embodiment of a plate that may be used as a fluid barrier in some embodiments of the moisture trap 130. As shown in FIG. 5, a plate 238 may include a collection end 248, a drainage end 250, a condensation surface 242, and one or more liquid channels 244. The plate 238 may be of a similar size, have similar properties, and operate in a manner similar to the plate 138 of FIG. 4A. As shown in FIG. 5, the liquid channels 244 may have additional shapes as desired to direct liquid as needed in the particular embodiment of the moisture trap 130.

In operation, the reduced-pressure source 108 can supply reduced pressure to the dressing 104 through the canister 106, drawing fluid from the tissue site 102 into the fluid reservoir 120 through the port 122. Fluid may be stored in the fluid reservoir 120 and fluid having evaporated liquid therein may be drawn into the moisture trap 130 through the opening 133. The filter 135 may prevent condensed liquid from passing from the fluid reservoir 120 into the moisture trap 130 so that fluid entering the moisture trap 130 may be composed primarily of gas and evaporated liquid.

The reduced-pressure source 108 can also draw the gas and evaporated liquid through the indirect fluid path provided by the moisture trap 130. Fluid having gas and evaporated liquid may be exposed to a surface of each plate 138 as it moves through the indirect fluid path of the moisture trap 130. For example, as fluid passes through the opening 133, the indirect fluid path formed by the plates 138 can direct fluid toward the top wall 131 forming the exterior of the canister 106 around the second end of the plate 138 and toward the second wall 134 so that the fluid on a first side of the plate 138 flows in an opposite direction from fluid flowing on a second side of the plate 138. In some embodiments, the indirect fluid path can move fluid in opposing directions on opposite sides of each plate 138.

The condensation surface 142 may be a portion of the plate 138 that is attractive to liquid so that liquid evaporated in fluid flowing adjacent to the condensation surface 142 of the plate 138 may be urged to condense from the fluid onto the condensation surface 142. As the gas and evaporated liquid flow across the condensation surfaces 142, the protrusions 146 and the hydrophilic properties of the condensation surfaces 142 can cause the evaporated liquid to condense onto the condensation surfaces 142. The protrusions 146 may aid in condensation by acting as preferential sites for nucleation that condenses liquid from the fluid passing by the condensation surface 142. The protrusions 146 may also aid in moving liquid condensed onto the condensation surface 142 toward the liquid channels 144. As liquid is condensed, the liquid may be urged toward the sump 140 by the liquid channels 144. If the liquid reaches the sump 140, the liquid may be trapped by the sump 140. In this manner, the liquid content of fluid leaving the canister 106 may be reduced.

Figure 6:
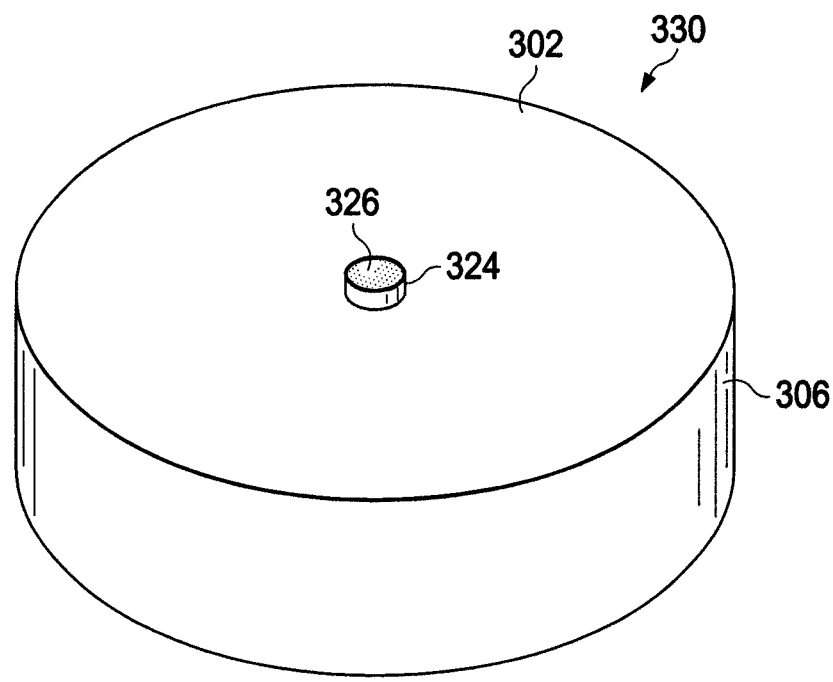
FIG. 6 is a perspective view of another illustrative embodiment of a moisture trap that may be used with the reduced-pressure therapy system of FIG. 1.
Figure 7:
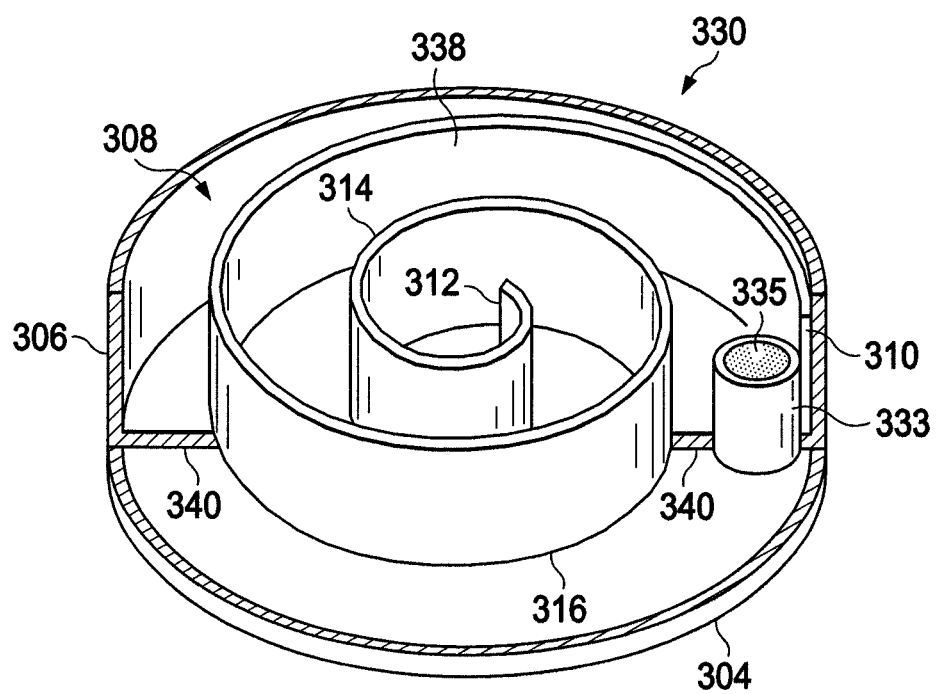
FIG. 7 is a partial sectional perspective view of the moisture trap of FIG. 6.

FIG. 6 is a perspective view illustrating another example embodiment of a moisture trap 330, and FIG. 7 is a cut-away view illustrating additional details of the moisture trap 330. The moisture trap 330 may operate in a manner similar to the moisture trap 130, modified as described in more detail below. In the illustrated embodiment, the moisture trap 330 may be a cylindrical body having a top wall 302, a bottom wall 304, and a cylindrical side wall 306. The cylindrical side wall 306 may be coupled to a peripheral portion of the bottom wall 304 and to a peripheral portion of the top wall 302. The top wall 302, the bottom wall 304, and the cylindrical side wall 306 form an interior 308, which can be fluidly isolated from an ambient environment.

The illustrative embodiment of the moisture trap 330 also may include a fluid inlet 333 and a fluid outlet 324. The fluid inlet 333 may be disposed proximate to the cylindrical side wall 306 and a peripheral portion of the bottom wall 304. The fluid outlet 324 may be disposed proximate to a center portion of the top wall 302 and be may generally be aligned with an axis of the moisture trap 330. Both the fluid inlet 333 and the fluid outlet 324 may be cylindrical bodies configured to be fluidly coupled to a conduit so that the moisture trap 330 may be disposed in a fluid path between a fluid reservoir and a reduced-pressure source. For example, the moisture trap 330 may be fluidly coupled between the fluid reservoir 120 of the canister 106 and the reduced-pressure source 108 of FIG. 1. Filters 335 and 326 may also be disposed within the fluid inlet 333 and the fluid outlet 324, respectively. The filters 335 and 326 may be similar to the filters 135 and 126 of FIG. 1, and may also be formed of a hydrophobic material. The fluid inlet 333 may have a cylindrical wall extending into the interior 308 from the bottom wall 304 so that a terminus of the fluid inlet 333 may be separated from an interior surface of the bottom wall 304.

The moisture trap 330 also may include a sump 340, which may be similar in many respects to the sump 140. In the illustrative embodiment of FIG. 7, for example, the sump 340 may be disposed adjacent to the bottom wall 304. The sump 340 may include a layer of absorbent material having a thickness less than the height of the cylindrical side wall 306 and may be coextensive with the bottom wall 304. In some embodiments, the thickness of the absorbent material may vary as needed for the particular application of the moisture trap 330. In some embodiments, the sump 340 may not be coextensive with the bottom wall 304 of the moisture trap 330 to allow the sump 340 to expand as the sump 340 receives liquid, for example. The sump 340 can be fluidly isolated from a fluid reservoir so that liquid in the fluid reservoir may not interact with the sump 340.

Liquid condensed from fluid flowing through the moisture trap 330 may primarily be water, making materials formed of super-absorbent polymers suitable for efficient use as the sump 340. In some embodiments the sump 340 may be sodium polyacrylate. In other embodiments, the sump 340 may be BASF Luquasorb® or Luquafleece® 402C; Technical Absorbents Limited superabsorbent fibers, such as TAL 2327; Texsus spa FP2325; or an isolyser. In still other embodiments, the sump 340 may be an absorbent having carboxymethyl cellulose or alginates.

The moisture trap 330 also may include a fluid barrier, such as a spiral barrier 338. The spiral barrier 338 may be similar to the plate 138 in some respects. The spiral barrier 338 may be an Archimedean spiral having a first end 310, a second end 312, and opposing lateral edges 314, 316. The spiral barrier 338 may have other spiral shapes such as Cornu, Fermat, hyperbolic, lituus, or logarithmic spirals, for example. The spiral barrier 338 may be disposed within the interior 308 so that the first end 310 may be proximate to the fluid inlet 333 and the second end 312 may be proximate to the fluid outlet 324. In the illustrated embodiment, the first end 310 may be adjacent to the cylindrical side wall 306 so that fluid may not flow between the first end 310 and the cylindrical side wall 306. In other embodiments, the first end 310 may be proximate to the cylindrical side wall 306 and allows fluid flow between the first end 310 and the cylindrical side wall 306. The opposing lateral edges 314, 316 may be coupled to the top wall 302 and the bottom wall 304, respectively, to prevent fluid communication between the opposing lateral edges 314, 316 and the top wall 302 and the bottom wall 304.

The spiral barrier 338 may also include condensation surfaces and liquid channels similar to the condensation surfaces 142 and the liquid channels 144 of the plate 138. The condensation surfaces may operate similar to the condensation surface 142 and the liquid channels may direct fluid to the sump 340 similar to the liquid channels 144. The condensation surfaces and the liquid channels may also be formed in a manner similar to the condensation surface 142 and the liquid channels 144.

The spiral barrier 338 may be a single member formed to have the spiral shape. The spiral barrier 338 may be manufactured by rolling a strip of a plate-like material to form the desired shape, for example. In some embodiments, a strip of material may be bent to form the desired shape. In still other embodiments, the spiral barrier 338 may be formed of multiple members joined to form the spiral shape.

In operation, fluid may enter the moisture trap 330 through the fluid inlet 333 proximate to the first end 310 of the spiral barrier 338, and may flow adjacent to the surface of the spiral barrier 338. The curve of the spiral barrier 338 may be adapted to direct fluid along a spiral path toward the second end 312 of the spiral barrier 338 proximate to the fluid outlet 324. In this manner, the spiral barrier 338 forms an indirect fluid path between the fluid inlet 333 and the fluid outlet 324 by changing the direction of the fluid as the fluid flows between the fluid inlet 333 and the fluid outlet 324. In some embodiments, as fluid flows adjacent to the spiral barrier 338, hydrophilic condensation surfaces may cause liquid to condense from the fluid onto the surface of the spiral barrier 338.

Figure 8:
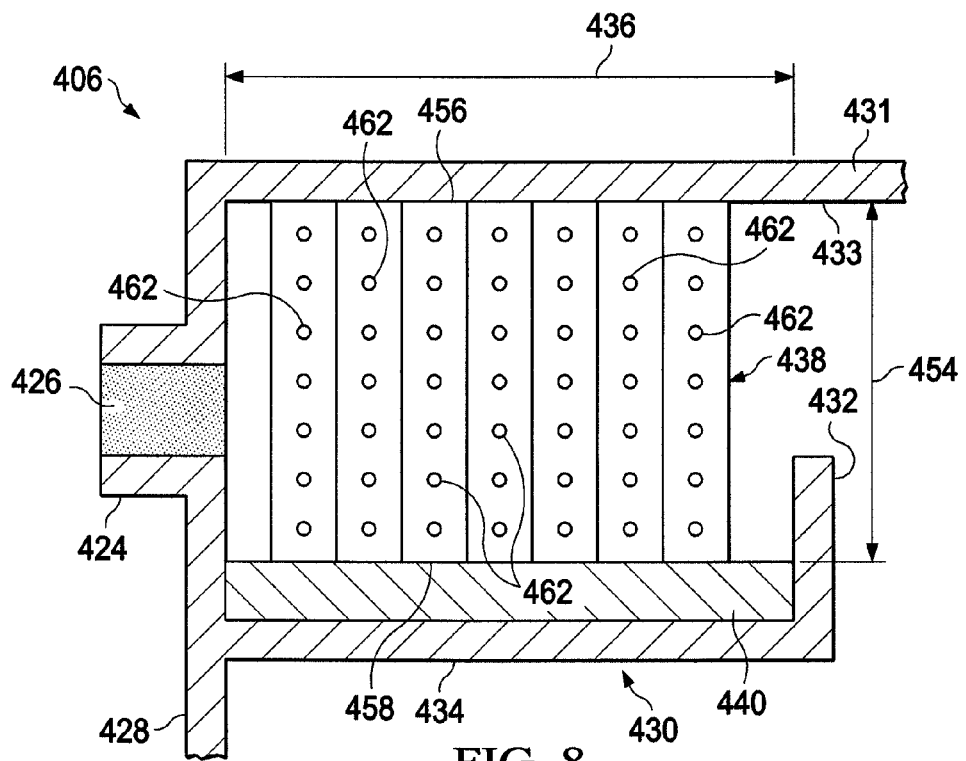
FIG. 8 is a detail sectional view of a portion of an illustrative canister having another embodiment of a moisture trap that may be used with the reduced-pressure therapy system of FIG. 1.

FIG. 8 is a partial sectional view illustrating details of another illustrative embodiment of a moisture trap 430 that may be associated with the therapy system 100. A portion of a canister 406 is also illustrated in FIG. 8, having the illustrative moisture trap 430 disposed therein. The canister 406 may be similar to the canister 106 in many respects, and generally may include a fluid outlet 424 having a filter 426 disposed therein. The fluid outlet 424 may be similar to and operate like the opening 124 and the fluid outlet 324, and the filter 426 may be similar to and operate like the filter 126 and the filter 326 described above. The canister 406 may include an end wall 428 and a top wall 431. The end wall 428 and the top wall 431 may be similar to and operate in a manner similar to the end walls 128 and the top and bottom walls 131 of FIG. 2. The example embodiment of the moisture trap 430 illustrated in FIG. 8 generally may include a first wall 432 and a second wall 434, which may be joined orthogonally. The second wall 434 may be joined at an opposite end to the end wall 428 of the canister 406. The first wall 432 may generally be parallel to the fluid outlet 424 and separated from the fluid outlet 424 by a distance 436. The distance 436 may be a portion of a total length of the canister 406. In some embodiments, the distance 436 may extend a majority of the length of the canister 406. In other embodiments, the distance 436 may extend less than about one-half of the length of the canister 406. The second wall 434 may generally be perpendicular to the first wall 432. Both the first wall 432 and the second wall 434 may have side ends perpendicular to the first end and the second end that join to the side walls forming the canister 406.

The first wall 432 may extend from the second wall 434 toward the top wall 431 of the canister 406 a portion of the distance between the second wall 434 and the top wall 431 of the canister 406. This may form an opening 433 that permits fluid communication between the moisture trap 430 and a fluid reservoir of the canister 406. In some embodiments, the first wall 432 may join the top wall 431 of the canister 406 and the opening 433 may be formed in the first wall 432 similar to the first wall 132 and the opening 133. A filter may be disposed within the opening 433. In the example embodiment of FIG. 8, the opening 433 does not have a filter.

The moisture trap 430 may also include a sump 440. In the illustrated embodiment, the sump 440 may be disposed adjacent to the second wall 434 and perpendicular to the first wall 432. The sump 440 may include an absorbent layer having a thickness less than the height of the first wall 432, and may be coextensive with the second wall 434 in some embodiments. In some embodiments, the thickness of the absorbent layer may vary as needed for the particular application of the moisture trap 430. In some embodiments, the sump 440 may extend only a portion of the second wall 434 of the moisture trap 430 to allow the sump 440 to expand as the sump 440 receives fluid, for example. The sump 440 can be fluidly isolated from the fluid reservoir in some embodiments so that liquid in the fluid reservoir may not interact with the sump 440.

Liquid condensed from the fluid flowing through the moisture trap 430 may primarily be water, making materials formed of super absorbent polymers suitable for efficient use as the sump 440. In some embodiments the sump 440 may be sodium polyacrylate. In other embodiments, the sump 440 may be BASF Luquasorb® or Luquafleece® 402C; Technical Absorbents Limited superabsorbent fibers, such as TAL 2327; Texsus spa FP2325; or an isolyser. In still other embodiments, the sump 440 may be an absorbent having carboxymethyl cellulose or alginates.

Figure 9:
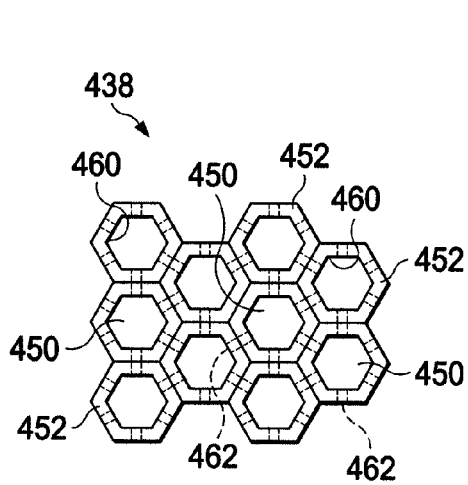
FIG. 9 is a top view of an example of cellular material that can be used with the moisture trap of FIG. 8.
Figure 10:
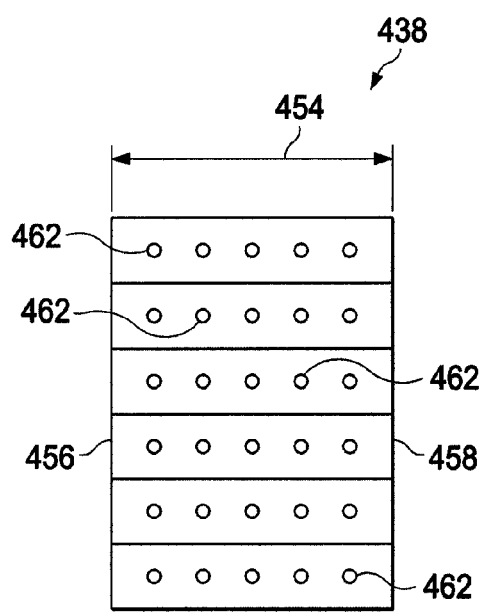
FIG. 10 is an elevation view of the cellular material of FIG. 9.

As illustrated in FIG. 8, the moisture trap 430 may also include a barrier, such as an array 438 of cells 450. FIG. 9 is a top view of the array 438, and FIG. 10 is side elevation view of the array 438, illustrating additional details that may be associated with some embodiments. The array 438 may include a cluster of individual cells 450 having cell walls 452. Generally, a cell, such as each cell 450, may be a component that may be combined with other substantially identical components to form a whole. The cell walls 452 of each cell 450 may be interconnected or shared with the cell walls 452 of adjacent cells 450 so that the plurality of cells 450 form the interconnected structure of the array 438. In the illustrated embodiment, each cell 450 may have a hexagonal shape with six cell walls 452. In other embodiments, each cell 450 may have a circular, square, triangular, rhomboidal, or amorphous shape. The cell walls 452 in the illustrative embodiment may each form a channel 460 extending through each cell 450 from a first end 456 to a second end 458. The cell walls 452 may have a length 454 so that each cell 450 may extend from the top wall of the top and bottom walls 431 of the canister 406 to the sump 440. Each channel 460 may be open at the second end 458 of the cell 450 so that the channel 460 may be in fluid communication with the sump 440. In some embodiments, the channel 460 may be open at the first end 456.

Each cell wall 452 may include a plurality of perforations 462. The perforations 462 may extend through the cell wall 452 so that fluid may communicate through the cell wall 452. In some embodiments, the perforations 462 may permit fluid communication between the channel 460 and an ambient environment, for example a fluid reservoir of the canister 406. The perforations 462 may also permit fluid communication between the channels 460 of adjacent cells 450 having an interconnected cell wall 452. In the illustrated embodiment, each cell 450 may have a distance between parallel sides, that is, across the flats, of about 6 mm. The size of the cells 450 may be reduced to increase the available surface area provided the by cell walls 452, thus increasing the ability of the cells 450 to cause condensation. In addition, the size of the cells 450 may be increased to reduce the flow restriction through the moisture trap 430, if desired.

The cells 450 may be formed of a thermoplastic and may have hydrophilic properties. In some embodiments, the cells 450 may be formed of a material such as those manufactured by Baltex, Plascore, Inc., or Hexacor Limited. In some embodiments, these materials may be referred to as a 3-D fabric. 3-D fabrics may be materials having the flexibility associated with fabric while having length, width, and depth. Some 3-D fabrics may be formed similar to the array 438 described above. Other 3-D fabrics may be formed having two layers of woven material joined by a plurality of fibers. The material may also be treated similar to the plate 138 to vary the hydrophilicty of the material as desired for the particular application of the array 438.

As shown in FIG. 8, the array 438 can be disposed between the sump 440 and the top wall 431 of the canister 406 so that the array 438 can provide a barrier to fluid flow between a fluid reservoir of the canister 406 and the fluid outlet 424. The array 438 may be coupled to the top wall 431 and side walls of the canister 406 so that the fluid path flows through the array 438. The fluid may flow through the array 438 by passing through the perforations 462 in each cell wall 452. In the illustrated embodiment, each cell 450 may be hexagonal and joined to at least two adjacent cells 450 so that the perforations 462 may not form a straight flow path from the opening 433 to the fluid outlet 424.

In operation, the reduced-pressure source 108 can supply reduced pressure to the dressing 104 through the canister 406, drawing fluid from the tissue site 102 into the canister 106. Fluid may be stored in a fluid reservoir of the canister 106 and fluid having evaporated liquid therein may be drawn into the moisture trap 430 through the opening 433. The reduced-pressure source 108 can also draw the gas and evaporated liquid through an indirect fluid path formed by the array 438. As fluid passes through a perforation 462 in a first cell wall 452 of a cell 450 the fluid may change direction to reach the fluid outlet 424. If fluid to passes through a perforation 462 in a first cell wall 452 and not change direction, the fluid flow should eventually abut the top wall 431, the side walls of the canister 406, or the second wall 434 before reaching the fluid outlet 424. The top wall 431 and the side walls of the canister 406 or the second wall 434 can cause a change in the direction of the fluid flow. In this manner, the plurality of cells 450 can form an indirect fluid path. The array 438 can provide a large condensation area by increasing the surface area that the fluid may contact as it passes through the moisture trap 430. As gas and evaporated liquid flow across the surfaces of the cells 450, evaporated liquid can condense onto the cell walls 452. As liquid is condensed, the liquid may be urged toward the sump 440 by the channels 460. If liquid reaches the sump 440, the liquid may be trapped by the sump 440. In this manner, the moisture content of fluid leaving the canister 406 may be reduced. In some embodiments, the sump 440 and the array 438 may be joined to form a multi-function fluid management laminate.

Figure 11:
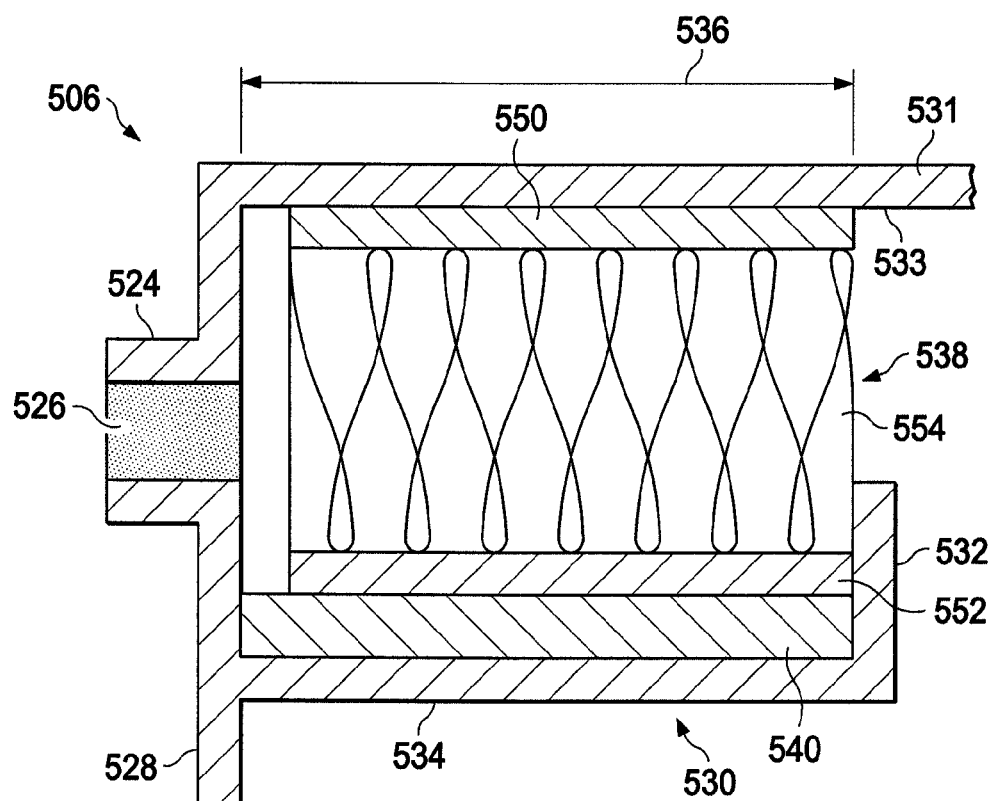
FIG. 11 is a detail sectional view of a portion of another illustrative canister having another example embodiment of a moisture trap that may be used with the reduced-pressure therapy system of FIG. 1.

FIG. 11 is a side sectional view illustrating another example embodiment of a moisture trap 530 disposed in a canister 506. The canister 506 may be similar to the canister 106 in many respects, modified as described below. The canister 506 in this example embodiment generally may include a fluid outlet 524 having a filter 526 disposed therein. The fluid outlet 524 may be similar to and operate like the opening 124, the fluid outlet 324, and the fluid outlet 424, and the filter 526 may be similar to and operate like the filter 126, the filter 326, and the filter 426 described above. The canister 506 may have an end wall 528 and a top wall 531. The end wall 528 and the top wall 531 may be similar to and operate in a manner similar to the end walls 128 and the top wall 131 of the canister 106 described above with respect to FIG. 2. The illustrative embodiment of the moisture trap 530 generally may include a first wall 532, a second wall 534, and a mesh barrier 538 having an upper layer 550, a lower layer 552, and a mesh layer 554. The first wall 532 and the second wall 534 may join at ends of each wall at an angle of approximately 90 degrees. The second wall 534 may be joined at an opposite end to the wall 528 of the canister 506. The first wall 532 may generally be parallel to the fluid outlet 524 and separated from the fluid outlet 524 by a distance 536. The distance 536 may be a portion of a total length of the canister 506. In some embodiments, the distance 536 may extend a majority of the length of the canister 506. In other embodiments, the distance 536 may extend less than about one-half of the length of the canister 506. The second wall 534 may generally be perpendicular to the first wall 532 and join the walls forming the canister 506 proximate to the fluid outlet 524. Both the first wall 532 and the second wall 534 have side ends perpendicular to the first end and the second end that may join to the side walls forming the canister 506. The first wall 532 may extend a portion of the perpendicular distance between the second wall 534 and the top wall 531 of the canister 506, forming an opening 533 that can permit fluid communication between the moisture trap 530 and a fluid reservoir of the canister 506. In some embodiments, the first wall 532 may join the top wall 531 of the canister 506 and the opening 533 can be formed in the first wall 532, similar to the first wall 432 and the opening 433. A filter may be disposed within the opening 533. In the illustrated embodiment, the opening 533 does not have a filter.

As illustrated, the example embodiment of the moisture trap 530 also may include a sump 540. The sump 540 may be disposed adjacent to the second wall 534 perpendicular to the first wall 532. The sump 540 may include a layer of absorbent material having a thickness less than the height of the first wall 532, and may be coextensive with the second wall 534. In some embodiments, the thickness of the absorbent material may vary as needed for the particular application of the moisture trap 530. In some embodiments, the sump 540 may not be coextensive with the second wall 534 of the moisture trap 530 to allow the sump 540 to expand as the sump 540 receives liquid, for example. In the illustrated embodiment, the sump 540 may be fluidly isolated from a fluid reservoir so that liquids in the fluid reservoir may not interact with the sump 540. The sump 540 may be an absorbent material disposed within the moisture trap 530 to collect liquid condensed from fluid flowing through the moisture trap 530.

Liquid condensed from fluid flowing through the moisture trap 530 may primarily be water, making materials formed of super-absorbent polymers suitable for efficient use as the sump 540. In some embodiments the sump 540 may be sodium polyacrylate. In other embodiments, the sump 540 may be BASF Luquasorb® or Luquafleece® 402C; Technical Absorbents Limited superabsorbent fibers, such as TAL 2327; Texsus spa FP2325; or an isolyser. In still other embodiments, the sump 540 may be an absorbent having carboxymethyl cellulose or alginates.

Figure 12:
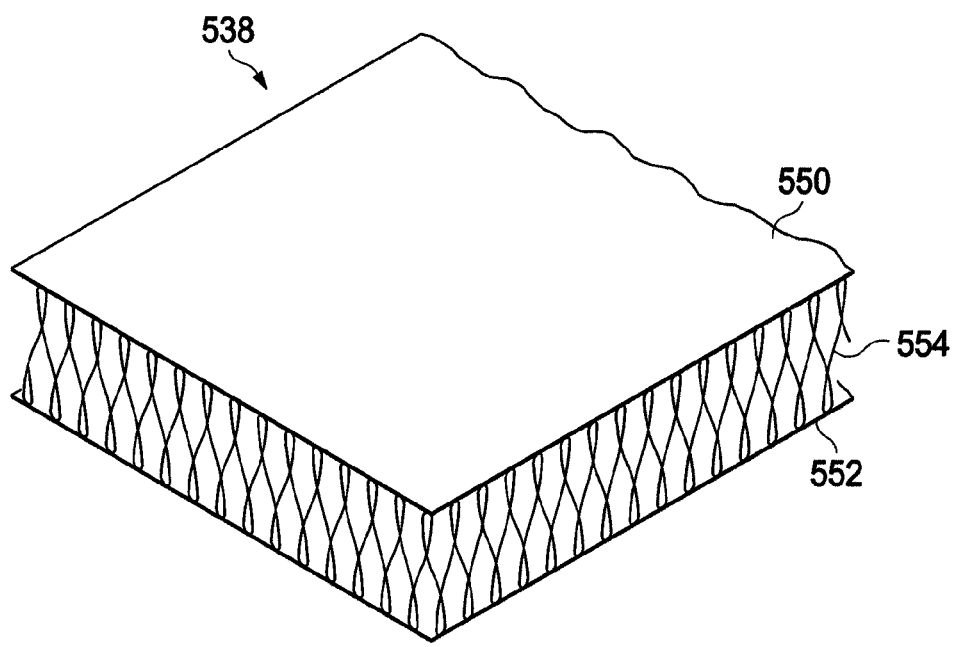
FIG. 12 is a perspective view of an example mesh material that can be used with the moisture trap of FIG. 11.

FIG. 12 is a perspective view illustrating additional details of the mesh barrier 538. The illustrative mesh barrier 538 of FIG. 12 generally may include the upper layer 550, the lower layer 552, and the mesh layer 554. The mesh barrier 538 may be oriented within the moisture trap 530 so that the upper layer 550 may be adjacent to the top wall 531 of the canister 506, and the lower layer 552 may be adjacent the sump 540. The mesh layer 554 can be disposed between and fluidly coupled to the upper layer 550 and the lower layer 552. The mesh barrier 538 may extend the entirety of the distance between the sump 540 and top wall 531. In some embodiments, the top wall 531 may be parallel to the sump 540 so that fluid flowing in the moisture trap 530 may flow through the mesh barrier 538. The upper layer 550 and the lower layer 552 may be wicking layers in some embodiments, configured to draw liquid into the mesh layer 554 or into the sump 540. The mesh layer 554 may be formed of a yarn, for example, which may be treated or coated to have hydrophilic properties. The yarn may be manufactured from different materials with different hydrophilic, hydrophobic, or absorbent properties. In addition, the type of yarn can also be varied to vary the width of the mesh layer 554 and the mesh barrier 538. In other embodiments, the mesh barrier 538 may be a spacer fabric produced by a knitting process, similar to those manufactured by Heathcoat Fabrics and Muler Textil. In one embodiment, the mesh barrier 538 may be a material formed of hydrophilic fibers formed of Nylon 6/6, such as polyester.

In operation, fluid can flow through the opening 533, encountering the mesh layer 554. The mesh layer 554 may be disposed in the fluid path between the opening 533 and the fluid outlet 524, causing fluid to flow in an indirect fluid path. Fibers forming the mesh layer 554 may cause fluid to make numerous changes of direction as fluid flows through the mesh layer 554. As fluid interacts with the mesh layer 554, hydrophilic properties of the mesh layer 554 may cause liquid to condense from the fluid. The mesh layer 554 may direct liquid along fibers of the mesh layer 554 into the lower layer 552. The lower layer 552 may wick liquid into the sump 540, where liquid can be stored. Fluid that may flow through the upper layer 550 may be directed into the mesh layer 554, where the mesh layer 554 may then cause liquid to condense from the fluid as described above.

The systems and methods described herein may provide significant advantages, some of which have already been mentioned. For example, the illustrative moisture traps can significantly reduce liquid content of fluid that exits a canister. The moisture traps may also prevent condensate from appearing in places where liquid should not be and prevent condensed liquid from providing a false perception that the device or canister may have been damaged or may be leaking. The moisture traps may also reduce the maintenance and service costs of a device. In many applications, the moisture traps can also make efficient use of a sump having a super-absorbent, as a super-absorbent sump can absorb more pure water condensed from fluid. In some embodiments, the moisture traps may also trap volatile organic compounds and other airborne particulates as liquid condenses. Some embodiments of the moisture traps may also help to dispose of fluidly contaminated components. Some embodiments of the moisture traps can be incorporated into a canister with minimal cost and may be retrofitted to other standard (Bemis type) canisters. Still further, some embodiments of the moisture traps may be replaceable with each canister.

It should be apparent from the foregoing that an invention having significant advantages has been described. While shown in only a few forms, the systems and methods illustrated are susceptible to various changes and modifications without departing from the spirit thereof.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment.

It will be understood that the benefits and advantages described above may relate to one embodiment or may relate to several embodiments. The operations described herein may be carried out in any suitable order, or simultaneously where appropriate.

Where appropriate, features of any of the embodiments described above may be combined with features of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site with reduced pressure, the system comprising:
   a dressing adapted to be placed adjacent to the tissue site;
   a reduced-pressure source adapted to be fluidly coupled to the tissue site;
   a canister having a fluid reservoir adapted to be fluidly coupled to the dressing and the reduced-pressure source; and
   a moisture trap disposed in the canister and fluidly separating a portion of the fluid reservoir, the moisture trap comprising a barrier and a sump adapted to receive condensation from the barrier, the barrier having a hydrophilic surface and defining an indirect fluid path between the fluid reservoir and the reduced-pressure source.

2. The system of claim 1, wherein:
   the barrier comprises plates in parallel juxtaposition and separated to define the indirect fluid path.

3. The system of claim 1, wherein:
   the barrier comprises plates in parallel juxtaposition and positioned to define the indirect fluid path; and
   each of the plates is disposed in a plane that intersects with the sump.

4. The system of claim 1, wherein:
   the barrier comprises solid plates in parallel juxtaposition and positioned to define the indirect fluid path; and
   each of the solid plates is disposed in a plane that intersects the sump.

5. The system of claim 1, wherein:
   the barrier comprises a plate configured to direct fluid in opposing directions on opposing sides of the plate.

6. The system of claim 1, wherein the hydrophilic surface comprises one or more protrusions.

7. The system of claim 1, wherein the hydrophilic surface comprises one or more protrusions in the range of about 15 micrometers to about 20 micrometers.

8. The system of claim 1, wherein the barrier further comprises a channel adapted to direct condensation to the sump.

9. The system of claim 1, wherein the barrier further comprises a hydrophobic channel adapted to direct condensation to the sump.

10. The system of claim 1, wherein the barrier further comprises a hydrophobic channel adapted to direct condensation to the sump, and the hydrophilic surface comprises protrusions adapted to direct condensation to the hydrophobic channel.

11. The system of claim 1, wherein the barrier comprises a spiral barrier having lateral edges coupled to the moisture trap, a first end disposed proximate to the fluid reservoir, and a second end disposed proximate to the reduced-pressure source.

12. The system of claim 1, wherein the barrier comprises cells having interconnected cell walls, the cell walls having perforations defining the indirect fluid path.

13. The system of claim 1, wherein the barrier comprises cells having interconnected cell walls, each cell having a hexagonal shape, and the cell walls having perforations defining the indirect fluid path.

14. The system of claim 1, wherein the barrier comprises cells having interconnected cell walls, each cell having a hexagonal shape having a distance across a flat of about 6 mm, and the cell walls having perforations defining the indirect fluid path.

15. The system of claim 1, wherein the barrier comprises a mesh having an upper layer, a lower layer, and fibers coupled between the upper layer and the lower layer, the indirect fluid path defined by spaces between the fibers.

16. The system of claim 1, wherein the sump comprises an absorbent.

17. The system of claim 1, wherein the moisture trap is disposed within the fluid reservoir of the canister and adjacent to a fluid outlet of the canister so that fluid flowing through the canister passes through the moisture trap.

18. The system of claim 1, wherein the barrier comprises a hydrophilic material having a hydrophobic material disposed thereon to form a liquid channel.

19. The system of claim 1, wherein the barrier comprises a hydrophobic material having a hydrophilic material coated thereon, areas of the hydrophobic material that are uncoated forming a liquid channel.

20. The system of claim 1, wherein the barrier comprises a hydrophilic portion and a hydrophobic portion, the hydrophobic portion forming a liquid channel, and the hydrophilic portion comprising greater than or equal to about 80% of the barrier.

21. The system of claim 1, wherein the moisture trap further comprises a fluid inlet having a hydrophobic filter disposed thereon so that fluid flowing through the fluid inlet passes through the hydrophobic filter.

22. The system of claim 1, wherein the moisture trap further comprises a fluid outlet having a hydrophobic filter disposed thereon so that fluid flowing through the fluid outlet passes through the hydrophobic filter.

23. The system of claim 1, wherein the moisture trap further comprises:
   a fluid inlet having a hydrophobic filter disposed thereon so that fluid flowing through the fluid inlet passes through the hydrophobic filter; and
   a fluid outlet having a hydrophobic filter disposed thereon so that fluid flowing through the fluid outlet passes through the hydrophobic filter.

24. A moisture trap for removing liquid from fluid in a reduced pressure treatment system, the moisture trap comprising:
  a fluid inlet configured to be fluidly coupled to a reduced-pressure inlet of a canister;
  a fluid outlet configured to be fluidly coupled to a reduced-pressure source;
  a barrier disposed between the fluid inlet and the fluid outlet to provide an indirect fluid path between the fluid reservoir and the reduced-pressure source, the barrier having a hydrophilic surface; and
  a sump adapted to receive condensation from the barrier;
  wherein the moisture trap forms a separately enclosed space within the canister.

25. The moisture trap of claim 24, wherein the barrier comprises plates in parallel juxtaposition and positioned to define the indirect fluid path.

26. The moisture trap of claim 24, wherein:
  the barrier comprises plates in parallel juxtaposition and positioned to provide the indirect fluid path; and
  each of the plates is disposed in a plane that intersects the sump.

27. The moisture trap of claim 24, wherein:
  the barrier comprises solid plates in parallel juxtaposition and positioned to provide the indirect fluid path; and
  each of the solid plates is disposed in a plane that intersects the sump.

28. The moisture trap of claim 24, wherein the barrier comprises plates in parallel juxtaposition and configured to direct fluid in opposing directions on opposing sides of each plate.

29. The moisture trap of claim 24, wherein the hydrophilic surface comprises one or more protrusions.

30. The moisture trap of claim 24, wherein the hydrophilic surface comprises one or more protrusions in the range of about 15 micrometers to about 20 micrometers.

31. The moisture trap of claim 24, wherein the barrier further comprises a channel adapted to direct condensation to the sump.

32. The moisture trap of claim 24, wherein the barrier further comprises a hydrophobic channel adapted to direct condensation to the sump.

33. The moisture trap of claim 24, wherein the barrier further comprises a hydrophobic channel adapted to direct condensation to the sump, and the hydrophilic surface comprises protrusions adapted to direct condensation to the hydrophobic channel.

34. The moisture trap of claim 24, wherein the barrier comprises a spiral barrier having a first end disposed proximate to the fluid inlet and a second end disposed proximate to the fluid outlet.

35. The moisture trap of claim 24, wherein the barrier comprises cells having interconnected cell walls, the cell walls having perforations to provide the indirect fluid path.

36. The moisture trap of claim 24, wherein the barrier comprises cells having interconnected cell walls, each cell having a hexagonal shape, and the cell walls having perforations providing the indirect fluid path.

37. The moisture trap of claim 24, wherein the barrier comprises a mesh having an upper layer, a lower layer, and fibers coupled between the upper layer and the lower layer, the indirect fluid path provided by spaces between the fibers of the mesh.

38. The moisture trap of claim 24, wherein the sump comprises an absorbent.

39. The moisture trap of claim 24, wherein the barrier comprises a hydrophilic material having a hydrophobic material disposed thereon to form a liquid channel.

40. The moisture trap of claim 24, wherein the barrier comprises a hydrophobic material having a hydrophilic material coated thereon, areas of the hydrophobic material that are uncoated forming a liquid channel.

41. The moisture trap of claim 24, wherein the barrier comprises a hydrophilic portion and a hydrophobic portion, the hydrophobic portion forming a liquid channel, and the hydrophilic portion comprising greater than or equal to about 80% of the barrier.

42. The moisture trap of claim 24, further comprising a hydrophobic filter disposed in the fluid inlet so that fluid flowing through the fluid inlet passes through the hydrophobic filter.

43. The moisture trap of claim 24, further comprising a hydrophobic filter disposed in the fluid outlet so that fluid flowing through the fluid outlet passes through the hydrophobic filter.

44. The moisture trap of claim 24, further comprising:
  a first hydrophobic filter disposed in the fluid inlet so that fluid flowing through the fluid inlet passes through the hydrophobic filter; and
  a second hydrophobic filter disposed in the fluid outlet so that fluid flowing through the fluid outlet passes through the hydrophobic filter.

45. A method for treating a tissue site with reduced pressure, the method comprising:
  disposing a dressing adjacent to the tissue site;
  fluidly coupling a reduced-pressure source to the reduced-pressure dressing;
  drawing fluid from the tissue site with the reduced-pressure source;
  collecting the fluid in a fluid reservoir fluidly coupled between the dressing and the reduced-pressure source;
  moving the fluid through a moisture trap forming a separate fluid volume in the fluid reservoir in an indirect fluid path between the fluid reservoir and the reduced-pressure source, wherein the indirect fluid path is formed by a barrier having a hydrophilic surface adapted to condense liquid from the fluid; and
  channeling the liquid from the hydrophilic surface to a sump.

46. The method of claim 45, wherein the indirect fluid path comprises a plurality of protrusions formed in the hydrophilic surface.

47. A method of manufacturing a moisture trap for a reduced-pressure therapy system, the method comprising:
  providing a fluid inlet configured to be fluidly coupled to a reduced-pressure inlet of a fluid reservoir;
  providing a fluid outlet configured to be fluidly coupled to a reduced-pressure source;
  forming a barrier having a hydrophilic surface;
  positioning the barrier between the fluid inlet and the fluid outlet to define an indirect fluid path between the fluid reservoir and the reduced-pressure source; and
  positioning the barrier within a separately enclosed space in the fluid reservoir, between the fluid inlet and the fluid outlet to define an indirect fluid path between the fluid reservoir and the reduced-pressure source; and
  positioning a sump to receive liquid condensed by the barrier.

48. The method of claim 47, wherein forming the barrier further comprises positioning plates in parallel juxtaposition and to define the indirect fluid path.

49. The method of claim 47, wherein:
  forming the barrier further comprises positioning plates in parallel juxtaposition to define the indirect fluid path; and
  disposing each of the plates in a plane that intersects the sump.

50. The method of claim 47, wherein:
  forming the barrier further comprises positioning solid plates in parallel juxtaposition to define the indirect fluid path; and
  disposing each of the solid plates in a plane that intersects the sump.

51. The method of claim 47, wherein forming the barrier further comprises positioning plates in parallel juxtaposition and configuring the plates to direct fluid in opposing directions on opposing sides of each plate.

52. The method of claim 47, wherein forming the barrier further comprises forming protrusions on the hydrophilic surface.

53. The method of claim 47, wherein forming the barrier further comprises forming protrusions on the hydrophilic surface, wherein the protrusions range between about 15 micrometers to about 20 micrometers.

54. The method of claim 47, wherein forming the barrier further comprises forming a channel adapted to direct condensation to the sump.

55. The method of claim 47, wherein forming the barrier further comprises forming a hydrophobic channel adapted to direct condensation to the sump.

56. The method of claim 47, wherein forming the barrier further comprises forming a hydrophobic channel adapted to direct condensation to the sump, and forming protrusions on the hydrophilic surface adapted to direct condensation to the hydrophobic channel.

57. The method of claim 47, wherein forming the barrier further comprises forming a spiral barrier having a first end disposed proximate to the fluid reservoir and a second end disposed proximate to the reduced-pressure source.

58. The method of claim 47, wherein forming the barrier further comprises forming cells having interconnected cell walls, and forming perforations in the cell walls to define the indirect fluid path.

59. The method of claim 47, wherein forming the barrier further comprises forming cells having interconnected cell walls, each cell having a hexagonal shape, and forming perforations on the cell walls to define the indirect fluid path.

60. The method of claim 47, wherein forming the barrier further comprises forming a mesh having an upper layer, a lower layer, and fibers coupled between the upper layer and the lower layer, and forming spaces between the fibers of the mesh to define the indirect fluid path.

61. The method of claim 47, wherein the sump comprises an absorbent.

62. The method of claim 47, wherein the barrier comprises a hydrophilic material and forming the barrier further comprises disposing a hydrophobic material on the barrier to form a channel.

63. The method of claim 47, wherein the barrier comprises a hydrophobic material and forming the barrier further comprises coating a hydrophilic material onto the hydrophobic material to form a channel, wherein areas of the hydrophobic material that are uncoated form the channel.

64. The method of claim 47, wherein forming the barrier further comprises forming each barrier with a hydrophilic portion and a hydrophobic portion, forming a channel with the hydrophobic portion, and wherein the hydrophilic portion comprises greater than or equal to about 80% of each barrier.

65. The method of claim 47, wherein the method further comprises disposing a hydrophobic filter in the fluid inlet so that fluid flowing through the fluid inlet passes through the hydrophobic filter.

66. The method of claim 47, wherein the method further comprises disposing a hydrophobic filter in the fluid outlet so that fluid flowing through the fluid outlet passes through the hydrophobic filter.

67. The method of claim 47, wherein the method further comprises:
  disposing a first hydrophobic filter in the fluid inlet so that fluid flowing through the fluid inlet passes through the hydrophobic filter; and
  disposing a second hydrophobic filter in the fluid outlet so that fluid flowing through the fluid outlet passes through the hydrophobic filter.

\* \* \* \* \*

UNITED STATES PATENT AND TRADEMARK OFFICE
CERTIFICATE OF CORRECTION

PATENT NO.           : 9,669,139 B2
APPLICATION NO.      : 14/186808
DATED                : June 6, 2017
INVENTOR(S)          : Richard Daniel John Coulthard et al.

Page 1 of 1

It is certified that error appears in the above-identified patent and that said Letters Patent is hereby corrected as shown below:

In the Claims

Column 22, Claim number 47, Line numbers 56-58, deleted "positioning the barrier between the fluid inlet and the fluid outlet to define an indirect fluid path between the fluid reservoir and the reduced-pressure source;"

Signed and Sealed this
Twenty-sixth Day of June, 2018

Andrei Iancu
*Director of the United States Patent and Trademark Office*